(12) United States Patent
Welch

(10) Patent No.: US 8,489,177 B2
(45) Date of Patent: Jul. 16, 2013

(54) FIDUCIAL MARKER AND METHOD FOR GAMMA GUIDED STEREOTACTIC LOCALIZATION

(75) Inventor: Benjamin Lawrence Welch, Hampton, VA (US)

(73) Assignee: Dilon Technologies, Inc., Newport News, VA (US)

( * ) Notice: Subject to any disclaimer, the term of this patent is extended or adjusted under 35 U.S.C. 154(b) by 1094 days.

(21) Appl. No.: 12/218,576

(22) Filed: Jul. 16, 2008

(65) Prior Publication Data
US 2010/0016713 A1 Jan. 21, 2010

(51) Int. Cl.
*A61B 6/02* (2006.01)

(52) U.S. Cl.
USPC ............ 600/436; 600/407; 600/425; 600/426

(58) Field of Classification Search
USPC .................................. 600/407, 425, 426, 436
See application file for complete search history.

(56) References Cited

U.S. PATENT DOCUMENTS

| | | | | |
|---|---|---|---|---|
| 4,250,392 A | * | 2/1981 | Leask et al. | 250/505.1 |
| 4,571,617 A | * | 2/1986 | Hasili | 348/180 |
| 5,397,329 A | | 3/1995 | Allen | |
| 5,855,554 A | * | 1/1999 | Schneider et al. | 600/407 |
| 6,060,712 A | | 5/2000 | Morgan et al. | |
| 6,102,516 A | | 8/2000 | Gibson | |
| 6,205,347 B1 | | 3/2001 | Morgan et al. | |
| 6,333,971 B2 | | 12/2001 | McCrory et al. | |
| 6,424,693 B1 | * | 7/2002 | Weisenberger | 378/37 |
| 6,927,406 B2 | * | 8/2005 | Zyromski | 250/496.1 |
| 2004/0054248 A1 | * | 3/2004 | Kimchy et al. | 600/3 |
| 2005/0276377 A1 | * | 12/2005 | Carol | 378/65 |
| 2006/0078502 A1 | * | 4/2006 | Dewanjee | 424/9.361 |
| 2006/0116633 A1 | * | 6/2006 | Shachar | 604/95.01 |
| 2007/0238950 A1 | | 10/2007 | Vija et al. | |
| 2008/0029705 A1 | * | 2/2008 | Tsuchiya et al. | 250/363.1 |
| 2008/0050311 A1 | * | 2/2008 | Goldenberg et al. | 424/1.49 |

OTHER PUBLICATIONS

Welch et al. "Quality Assurance Procedure for a Gamma Guided Stereotactic Breast Biopsy System." Physica Medica. pp. 102-105. 2006.*

* cited by examiner

*Primary Examiner* — Tse Chen
*Assistant Examiner* — Mark Remaly

(57) ABSTRACT

A fiducial marker for use in a gamma-guided stereotactic localization system for imaging a suspected cancer and guiding a physician in the removal of tissue samples for biopsy. The fiducial marker includes a fiducial source that can be accurately located in a positioning system and used to correlate the location of the positioning system with the detector and therefore the region-of-interest. The fiducial can be made radioactive such that it can be seen by the gamma camera. The fiducial marker enables the accurate positioning of other hardware in proximity to the object to be viewed.

12 Claims, 5 Drawing Sheets

FIDUCIAL MARKER AND METHOD FOR GAMMA GUIDED STEREOTACTIC LOCALIZATION

FIELD OF THE INVENTION

This invention relates to imaging of suspected cancer and specifically to a novel fiducial marker for a gamma guided stereotactic localization system that improves the accuracy of locating suspected cancers and provides an accurate tool in guiding a physician in the removal of tissue samples for biopsy.

BACKGROUND OF THE INVENTION

Mammographic imaging is well established as the primary screening modality for breast cancer. A suspicious finding on a mammographic examination may lead to imaging with another modality to further investigate the suspicious finding and ultimately to a biopsy being performed to confirm that cancer is or is not present. The other modalities may include a diagnostic mammogram, an ultrasound (US) examination, a magnetic resonance imaging (MRI) procedure, or a nuclear medicine procedure (known as scintimammography). Depending on the nature of the finding and the imaging system with which it was found, the surgeon or radiologist may be guided in the removal of tissue for pathological examination by one of these imaging systems. Breast biopsy systems have been produced and marketed which rely on x-ray guidance, US guidance, and MRI guidance.

Mammograms are x-rays that image tissue densities, not cancer activity. As a result, it can be difficult to identify cancerous lesions using mammography, especially when patients have dense breast tissue, multiple suspicious lesions, clusters of microcalcifications, palpable lesions not detected by mammography or ultrasound, post-surgical or post-therapeutic mass, implants, or have been taking Hormone Replacement Therapy.

MRI has shown usefulness as a next-step imaging modality for difficult-to-diagnose cases. Much like x-ray mammography, breast MRI relies on anatomical or structural information, but provides much more detailed images. It is limited, however, by its highly variable specificity, which can range from below 37% to 97%. Combined with its high sensitivity, it is expensive, may require multiple days to complete, and produces a high false positive rate.

Ultrasound is also commonly utilized as a next-step after a questionable mammogram and is good at determining if a suspect mass is solid or fluid-filled. However, ultrasound demonstrates a low specificity rate that can produce misleading results and indicate biopsy where one may not be needed.

Although biopsy systems employing x-ray, ultrasound, and MRI modalities exist, there remains a need for achieving further accuracy in determining the location of potentially cancerous lesions and for the accurate guidance of biopsy systems to the cancerous lesions.

SUMMARY OF THE INVENTION

The invention is a novel fiducial marker for use in a gamma-guided stereotactic localization system for imaging a suspected cancer and guiding a physician in the removal of tissue samples for biopsy. The fiducial marker includes a fiducial source that can be accurately located in a positioning system and used to correlate the location of the positioning system with the detector and therefore the region-of-interest. The fiducial can be made radioactive such that it can be seen by the gamma camera. The fiducial marker enables the accurate positioning of other hardware, such as biopsy needles or surgical equipment, in proximity to the object to be viewed.

OBJECT OF THE INVENTION

It is therefore an object of the present invention to provide a fiducial device for improving the accuracy of a stereotactic localization system for determining the extent of a primary lesion, detecting occult secondary lesions, and evaluating the axillary region for node status in breast cancer patients.

Another object of the present invention is to provide a fiducial source that can be imaged by a gamma camera.

A further object of the present invention is to provide a fiducial source that includes a measured quantity of a specific activity of radioactive substance for imaging by a gamma camera.

It is an object of the present invention to provide a gamma guided stereotactic localization that utilizes a fiducial marker to improve accuracy in imaging cancer activity.

It is a further object of the present invention to provide a fiducial marker for a gamma imaging system that images cancer activity rather than imaging tissue structure such as in x-ray, MRI, or ultrasound imaging techniques.

A further object of the present invention is to provide a fiducial source that is conveniently housed in a container for use in a positioning system of a gamma camera.

It is a further object of the present invention to provide a complementary diagnostic procedure to mammography that has greater sensitivity and specificity in identifying cancerous lesions.

A further object of the present invention is to provide an improved positioning system including a fiducial source for placing a biopsy needle accurately at an identified region of interest.

These and other objects and advantages of the present invention will be better understood by reading the following description along with reference to the drawings.

TABLE OF NOMENCLATURE

Figure 1:
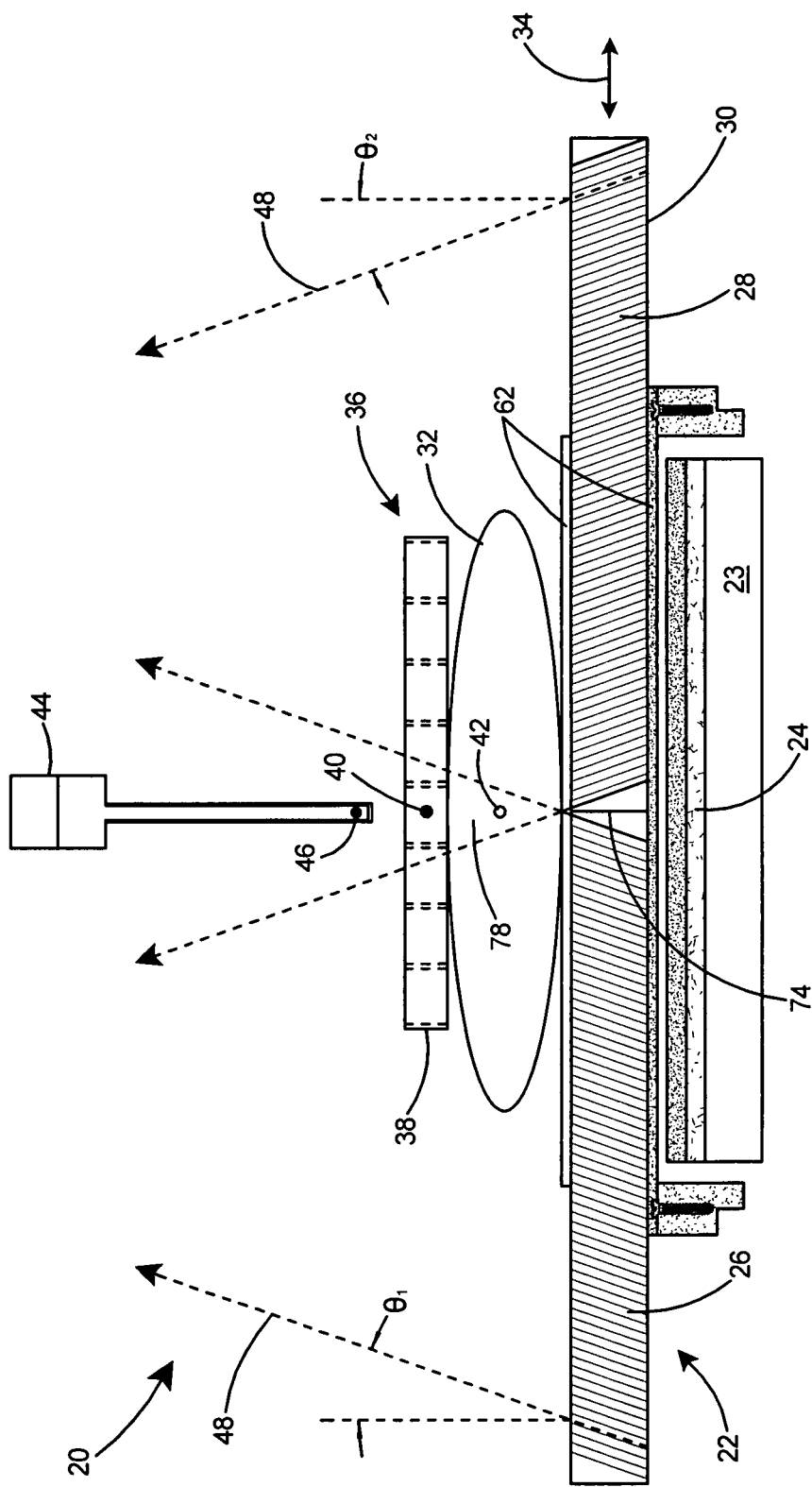
FIG. 1 is a conceptual front view of a preferred embodiment of a gamma guided stereotactic localization system according to the present invention including a gamma camera crystal, a stereo imaging system including a set of oppositely viewing slant-hole collimators, and a grid localization system with a fiducial marker source.

The following is a listing of part numbers used in the drawings along with a brief description:

20 gamma guided stereotactic localization system
22 stereo imaging system
23 gamma camera
24 gamma camera crystal
26 first or left side slant-hole collimator
28 second or right side slant-hole collimator
30 collimator set
32 object to be imaged or body part
34 direction of travel of collimator set
36 positioning system
38 grid localization system or grid localization plate
40 fiducial source or marker
42 region of interest
44 biopsy needle guide
46 gamma emitting marker source or obturator
48 camera viewing lines
50 grid support structure
52 cavity or fiducial recess
54 grid
56 grid opening
58 row in grid
60 column in grid
62 cassette
64 rectangular fiducial source container
66 circular fiducial source container
$\Theta_1$ stereotactic viewing angle of left slant-hole collimator
$\Theta_2$ stereotactic viewing angle of right slant-hole collimator

DETAILED DESCRIPTION OF THE INVENTION

Gamma guided stereotactic localization uses two gamma camera images of an object taken at different angles to determine the three dimensional location of the region of interest in that object, relative to the camera system. In some situations it is desirable to correlate the location of the region relative to the camera with the location of the region in the object and to have a gamma guided positioning system that can be used to support and accurately position other hardware in the vicinity of the object. Once the location is correlated with the object, it can be used, for example, for positioning a needle in a suspected tumor to collect a tissue sample for biopsy. In order to be imaged by the gamma camera, these markers must be radioactive and the marker must be seen in the image of the object.

Figure 2:
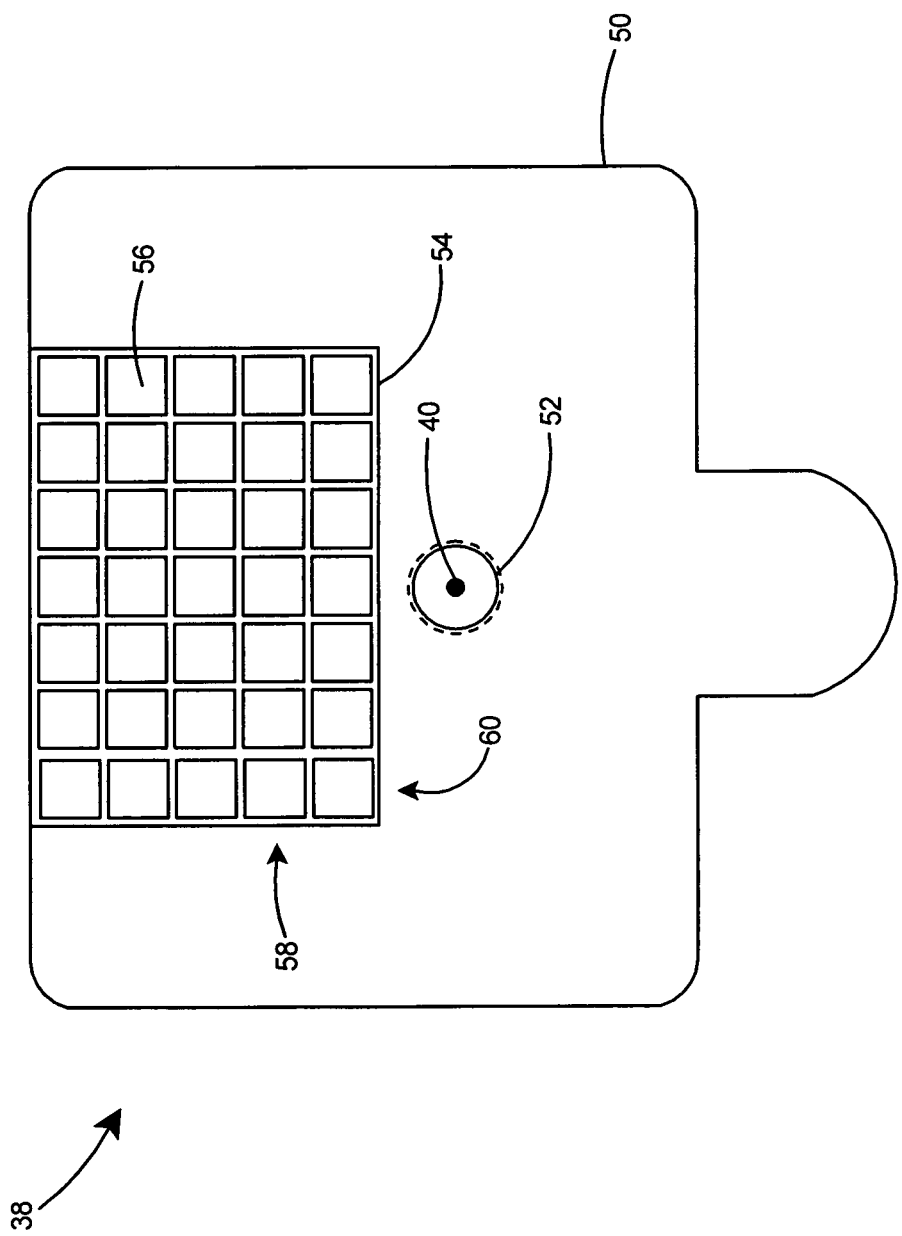
FIG. 2 is a top view of the grid localization system that forms a portion of the gamma guided stereotactic localization system of FIG. 1.

The present invention is a fiducial marker that can be placed in the positioning system to render it visible to the gamma camera. The positioning system is placed adjacent to the object to be imaged and held rigidly in place. The location of the fiducial relative to the camera system is calculated from the gamma camera images. The location of the region-of-interest relative to the camera system is then calculated from the gamma camera images. The location of the region-of-interest relative to the fiducial marker can then be calculated. After the location of the region-of-interest relative to the fiducial marker is known, the positioning system can be used to accurately position and support any other hardware that needs to be positioned at the region-of-interest by measurements from the fiducial marker. A diagram depicting this concept is given in FIG. 1, showing the gamma guided stereotactic localization system 20 with grid localization system 38 and fiducial source 40, the gamma camera crystal 24, and the stereo imaging system 22. A top view of the grid localization system 38 with fiducial source 40 is shown in FIG. 2.

In a gamma guided localization system, it is highly desirable to correlate the location of the region relative to the camera with the location of the region in the object and to provide a positioning system that can be used to support and accurately position other hardware in the vicinity of the object. Once the location is correlated with the object, it can be used, for example, for positioning a needle in a suspected tumor to collect a tissue sample for biopsy.

The present invention provides a fiducial source that can be inserted into the positioning system of a gamma guided stereotactic localization system for accurately locating and guiding biopsy equipment to cancerous lesions. A gamma guided stereotactic localization system is a functional or molecular breast imaging procedure that captures the metabolic activity of breast lesions through radiotracer uptake. A small amount of tracing agent, such as Tc-99m with a gamma ray energy of 140 keV, is delivered to a patient, and in turn is absorbed by all cells in the body. The tracing agent emits invisible gamma rays, which are detected by a gamma camera and translated into a digital image of the breast. Due to the higher metabolic activity of cancerous cells, these cells absorb a greater amount of the tracing agent and are revealed as "hot spots." This molecular breast imaging technique can help doctors more reliably differentiate cancerous from non-cancerous cells. While other adjunct modalities, such as MRI and ultrasound, image the physical structure of the breast, gamma guided stereotactic localization captures the cellular functioning of the breast tissue.

Stereotactic localization uses two images of an object taken at different angles to determine the three dimensional location of a region-of-interest in that object, relative to the imaging system coordinates. It is desirable to have a gamma-guided localization system for use in the gamma imaging of suspected cancer to guide a physician in the removal of tissue samples for biopsy.

In an effort to reduce that chance for error in this localization system a means to verify that the calculated location does indeed correspond to the location of the lesion is also desirable. This requires a marker to be placed in the object and the imaging system used to image this marker at that location. That image can then be compared with the image of the region of interest. In order to be imaged by the gamma camera, these markers must be radioactive and the marker must be seen in the image of the object. The gamma guided stereotactic localization system with fiducial marker satisfies these requirements.

With reference to FIG. 1 there is shown a gamma guided stereotactic localization system 20 with an improved positioning system 36 having a fiducial source 40 therein. The gamma guided stereotactic localization system 20 includes a stereo imaging system 22 composed of a gamma camera 23 including a gamma camera crystal 24 and a set of oppositely viewing slant-hole collimators. A first or left side slant-hole collimator 26 and a second or right side slant-hole collimator 28 are coplanar with each other and joined at their ends to form a side-by-side collimator set 30 that is movable with respect to the gamma camera crystal 24 and the body part or object 32 to be imaged. The collimator set 30 is movable either to the left or right in FIG. 1 as shown by directional arrow 34. The positioning system 36 includes a grid localization system or grid localization plate 38 that is rigidly mounted above the object 32 to be imaged. The gamma-emitting fiducial source 40, which can be imaged by the stereo imaging system 22, is accurately mounted in the positioning system 36. The stereo imaging system 22 is used to accurately identify a region-of-interest 42, such as a suspected cancerous lesion, in the object 32 to be imaged. The positioning system 36 is placed adjacent to the object 32 to be imaged and is used to support and accurately position other hardware, such as the biopsy needle guide 44 shown in FIG. 1, in close proximity to the object 32. A marker source 46, shown in the end of the biopsy needle guide 44, can be inserted into the object 32 at the calculated location of the region of interest 42 or lesion and used to verify that the calculated location is the actual location of the lesion. As shown by the angles of the conceptual camera viewing lines 48 in FIG. 1, the stereotactic viewing angles $\Theta_1$ and $\Theta_2$ are at +/−20 degrees with respect to a line perpendicular to the face of the gamma camera crystal 24. Left side slant-hole collimator 26 therefore views at a 20 degree angle to the right and right side slant-hole collimator 28 views at a 20 degree angle to the left.

The stereotactic gamma-guided localization method with fiducial marker involves three steps including localization, correlation, and verification. As shown in FIG. 1, the localization system includes a gamma camera having a gamma crystal 24 with a set of slant-hole collimators 26 and 28 that serve as the stereo viewing system. The positioning system 36 includes a grid localization system 38 with a fiducial source 40 therein that is placed adjacent to the object 32 to be imaged and held rigidly in place. The verification system includes a gamma emitting marker 46 that can then be placed by a biopsy needle guide 44 or similar tool at the calculated location of the region of interest 42 and imaged by the stereo imaging system 22 to verify that the inserted marker 46 coincides with the region of interest 42.

The fiducial marker of the present invention improves the correlation of the positioning system 36 with the stereo imaging system 22 and therefore more accurately determines the region-of-interest 42. The location of the fiducial source 40 relative to the stereo imaging system 22 is calculated from the gamma camera images. The location of the region-of-interest 42 relative to the stereo imaging system 22 is then calculated to locate the region-of-interest 42 relative to the fiducial source 40. The positioning system 36 can then be used to accurately position and support any other hardware, such as the biopsy needle guide 44 shown in FIG. 1, which needs to be positioned at the region of interest 42, by measurements from the fiducial source 40. The marker source 46 is then be used to verify that the calculated location of the region of interest 42 corresponds to the actual location.

The improved gamma guided stereotactic localization technique utilizing a fiducial marker according to the present invention includes: 1) placing a measured quantity of a specific activity of radioactive substance into a suitable fiducial source container to be mounted in the positioning system, 2) mounting the container in the positioning system, 3) placing the positioning system adjacent to the object to be imaged, 4) taking a pair of stereo images of the object; 5) determining the location of the fiducial marker in each of the images and calculating the (X, Y and Z) location of the fiducial, 6) determining the location of the region-of-interest in each of the images and calculating the (X, Y and Z) location of the region of interest, 7) determining the location of the region-of-interest relative to the fiducial marker within the positioning system, and 8) using the positioning system to locate and support any other hardware that needs to be positioned at the region of interest.

With reference to FIG. 2 there is shown a top view of the grid localization system 38 that forms a portion of the gamma guided stereotactic localization system of the present invention. The grid localization system 38 includes a grid support or shield 50, a cavity 52 for accepting a fiducial source 40 therein, and a grid 54 with a plurality of grid openings 56 therein arranged in rows 58 and columns 60. The grid localization system 38 enables a qualified physician to perform a gamma guided breast biopsy using a standard breast biopsy needle kit. The grid shield 50 is typically used to immobilize the breast during an imaging procedure.

The grid localization system 38 is used to locate the area of the breast or other body part that is directly above the suspected lesion. The grid 54 will be correlated with the location of the lesion that has been determined during the localization procedure via the fiducial marker 40. The fiducial marker 40 is imaged at the same time as the lesion and the location of the lesion relative to the fiducial marker 40 is calculated. The grid localization system 38 will also serve to stabilize the biopsy needle system during the gamma guided breast biopsy procedure.

Figure 3:
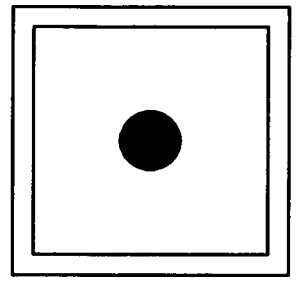
FIG. 3 is a top view of a rectangular shaped fiducial source that can be inserted into the grid support structure depicted in FIG. 2.
Figure 4:
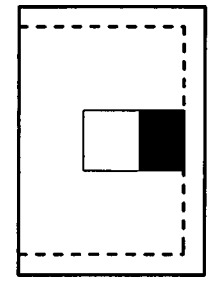
FIG. 4 is a phantom side view of the fiducial source of FIG. 3.

A first embodiment of a source container for a fiducial marker is depicted in FIGS. 3 and 4. The fiducial source container 64 is rectangular in shape and can be inserted into the grid support structure 50 shown in FIG. 2. This will allow the fiducial source container 64 to be positioned in a number of locations or grid openings 56 within the grid 54 and is very flexible in design. The fiducial source 40 can either be a solid long-lived radioactive source that is sealed permanently in the container and reused or a short-lived liquid source that is sealed in the container temporarily and then disposed of in an appropriate manner.

Figure 5:
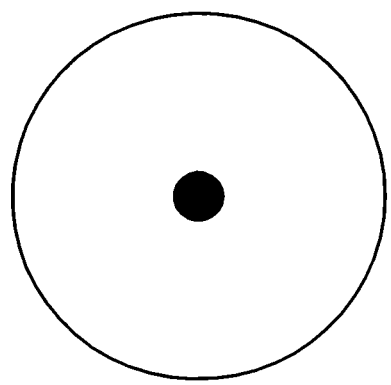
FIG. 5 is a top view of a circular shaped fiducial source that can be inserted into the circular hole in the grid support structure depicted in FIG. 2.
Figure 6:
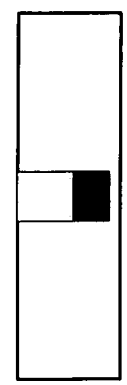
FIG. 6 is a phantom side view of the fiducial source of FIG. 5.

A second and preferred embodiment of the fiducial source container 66 is depicted in FIGS. 5 and 6. This fiducial source container 66 is circular in shape and can be inserted into the circular cavity 52 in the grid support structure 50 shown in FIG. 2. This will allow the fiducial source container 66 to be positioned at a known location in the grid support 50. The source can either be a solid long-lived radioactive source that is sealed permanently in the container and reused or a short-lived liquid source that is sealed in the container temporarily and then disposed of in an appropriate manner.

Figure 7:
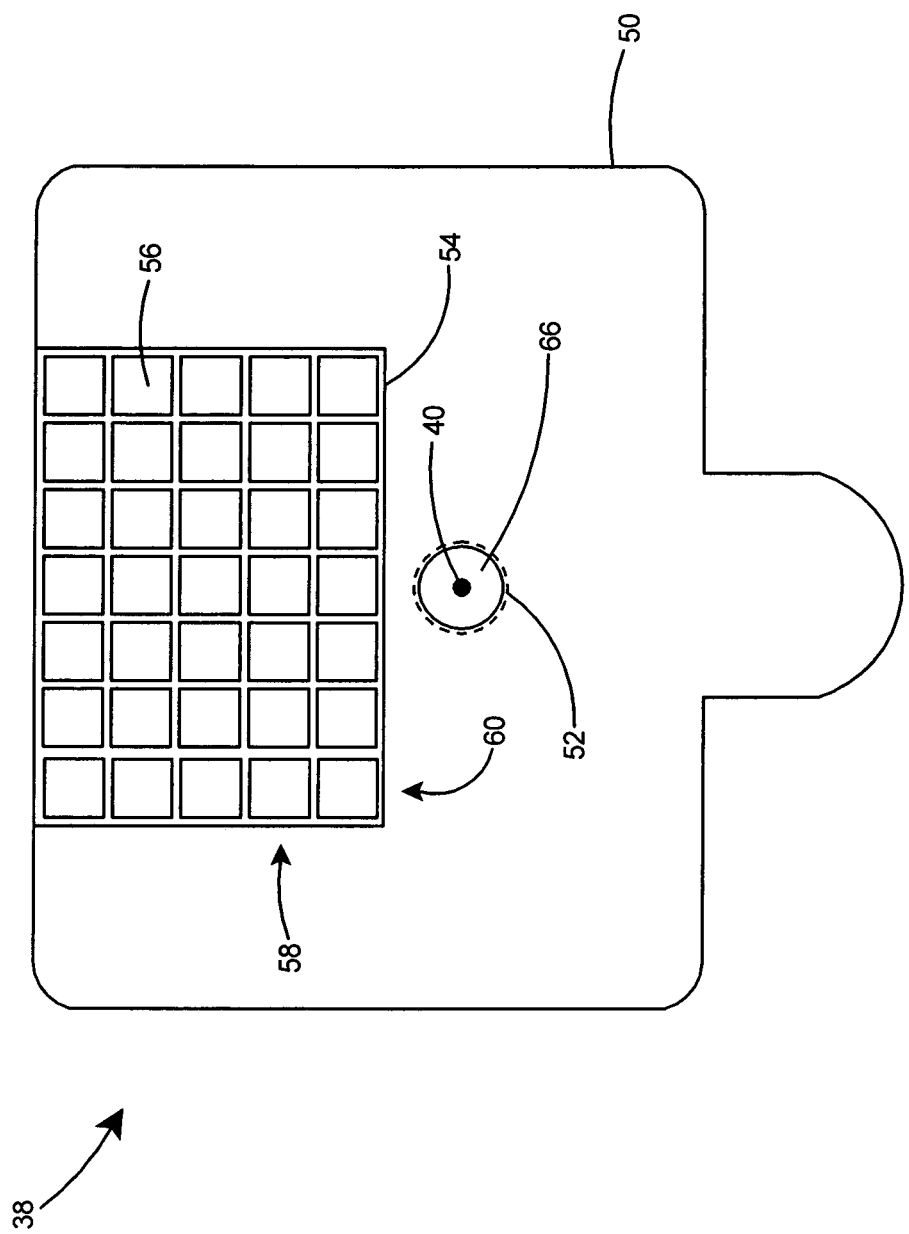
FIG. 7 is a top view of the grid localization system including a first embodiment of a fiducial source.

With reference to FIG. 7, there is shown a first arrangement of the grid localization system 38 in which a circular source container 66 including a fiducial marker 40 has been inserted into the cavity 52 in the grid support 50. The fiducial marker 40 is mechanically registered to the grid system and is used to correlate the location of the suspected lesion as determined by the stereo imaging system 22 and the grid localization system 38. This allows the physician to determine the location of the suspected lesion by measurements from the grid localization system 38.

Figure 8:
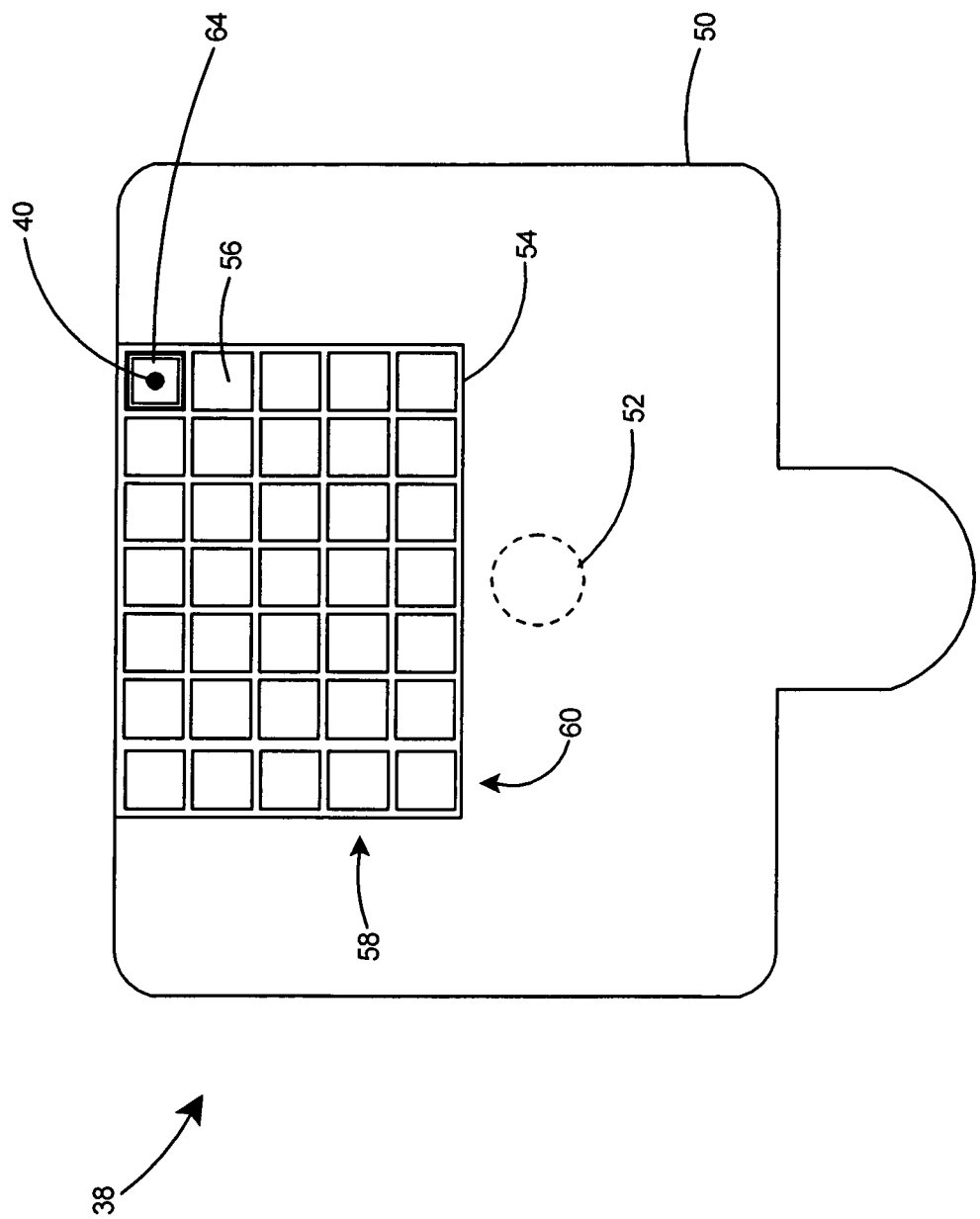
FIG. 8 is a top view of the grid localization system including a second embodiment of a fiducial source.

Referring to FIG. 8, there is an alternative arrangement of the grid localization system 38 in which a rectangular source container 64 including a fiducial marker 40 has been inserted into a grid opening 56 in the grid support 50. In this arrangement the fiducial marker 40 is also mechanically registered to the grid system and is used to correlate the location of the suspected lesion as determined by the stereo imaging system 22 and the grid localization system 38. The fiducial marker 40 enables the location of the suspected lesion to be determined with great accuracy.

Preferably, the activity level of the fiducial marker 40 is sufficient to be seen simultaneously with the lesion in the imaged object 32 (see FIG. 1) but low enough as to present no significant risk to the patient. Preferably, the fiducial marker 40 is a radioactive source of either Co-57 with a gamma ray energy of 122 keV or Ce-139 with a gamma ray energy of 160 keV. Preferably the specific activity of the Co-57 or Ce-139 is no less than 1 microcurie and no greater than 25 microcurie. Preferably, the gamma emitting fiducial source is an isotope having a gamma ray energy of at least 120 keV. Both Co-57 and Ce-139 are long lived sources that are reusable. The fiducial marker is typically refreshed annually or as indicated by an expiration date on the package. An alternative isotope is I-123, which is a short lived liquid but potentially useful if contained properly. The I-123 fiducial source is disposable.

Preferably the solid fiducial sources such as Co-57 or Ce-139 are hermetically sealed in epoxy or plastic. Alternatively, the solid sources could be sealed in containers constructed of aluminum or stainless steel. A liquid source fiducial would be loaded into a container on the day of the procedure, but not necessarily sealed.

As described above, the fiducial source of the present invention can be used to improve the accuracy of a gamma guided localization system. The radioactive fiducial source can be mounted in a positioning system of a stereo imaging system to improve the correlation of the location of the positioning system with the detector and therefore improve the accuracy in determining the exact location of the region-of-interest. The fiducial source of the present invention can be used with a gamma guided stereotactic localization system to produce stereo images from a compact gamma camera and to accurately determine the three dimensional location of a region of interest.

Although the description above contains many specific descriptions, materials, and dimensions, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. A fiducial marker in combination with a gamma detector for determining the location of a region-of-interest in a stationary object to be imaged comprising:
    a gamma guided positioning system located adjacent to and held rigidly in place on one side of said object to be imaged;
    a stereotactic imaging system mounted on an opposite side of said object to be imaged;
    said gamma guided positioning system including a grid localization plate having a plurality of grid openings therein;
    a gamma emitting fiducial source rigidly mounted in said gamma guided positioning system such that said fiducial source and said region-of-interest can be imaged simultaneously with said stereotactic imaging system;
    said stereotactic imaging system including a gamma camera having a gamma camera crystal and two oppositely viewing slant-hole collimators having parallel slant holes, wherein the collimators are coplanar to each other, configured to be positionable in a first image position and a second image position, and rigidly joined end to end thereby enabling said stereotactic imaging system to provide simultaneous views of a mutual overlap volume within said object;
    an algorithm for correlating the location of said gamma guided positioning system with said gamma camera and providing the location of said region-of-interest;
    said oppositely viewing slant-hole collimators including a left side slant-hole collimator viewing at a 20 degree angle to the right and a right side slant-hole collimator viewing at a 20 degree angle to the left;
    an arrangement for sliding said slant-hole collimators with respect to and in close proximity to said stationary object between the first image position and the second image position;
    said fiducial source including a radioactive substance having a specific activity of no less than 1 microcurie and no greater than 25 microcurie; and
    said fiducial source enabling accurate manipulation of said positioning system to support and guide diagnostic and surgical equipment to said region-of-interest.

2. The combination of claim 1 wherein said positioning system includes
    a biopsy needle guide and an obturator positioned above said grid localization plate; and
    a gamma emitting marker source in said obturator.

3. The combination of claim 2 wherein
    said grid openings in said grid localization plate arranged in rows and columns; and
    said grid localization plate including a cavity for accepting said fiducial source.

4. The combination of claim 1 wherein said gamma emitting fiducial source is Ce-139.

5. The combination of claim 1 wherein said gamma emitting fiducial source is an isotope having a gamma ray energy of 160 keV.

6. A method of locating and placing equipment at a region-of-interest in a stationary object to be imaged with a stereotactic imaging system including the steps of:
    providing a container and a positioning system, said positioning system including a grid localization plate having a plurality of grid openings therein, said grid localization plate adjustable in distance with respect to said stereotactic imaging system;
    placing a measured quantity of radioactive substance in said container to form a fiducial marker, said radioactive substance having a specific activity of no less than 1 microcurie and no greater than 25 microcurie;
    mounting said fiducial marker rigidly within said positioning system;
    providing a stereotactic imaging system mounted on an opposite side of said stationary object, said stereotactic imaging system including a gamma camera having a gamma camera crystal and two oppositely viewing slant-hole collimators having parallel slant holes, wherein the collimators are coplanar to each other, configured to be positionable in a first image position and a second image position, and rigidly joined end to end thereby enabling said stereotactic imaging system to provide simultaneous views of a mutual overlap volume within said object;
    mounting said positioning system in close proximity to and adjacent to the object to be imaged, positioning the collimators in a first image position and obtaining a first image, and positioning the collimators in a second image position and obtaining a second image, the first and the second images being a pair of stereo images of the object;
    determining the location of the fiducial marker in each of the images;
    calculating the X, Y, and Z coordinates of the fiducial marker;
    determining the location of the region-of-interest in each of the images;
    calculating the X, Y, and Z coordinates of the region-of-interest;
    determining the location of the region-of-interest relative to the fiducial marker within the positioning system; and
    guiding additional equipment to the region-of-interest based upon said calculated coordinates.

7. The method of claim 6 wherein said radioactive substance is Ce-139.

8. The method of claim 6 wherein said gamma emitting fiducial source is an isotope having a gamma ray energy of 160 keV.

9. The method of claim 6 wherein
said grid openings in said grid localization plate are arranged in rows and columns;
and said grid localization plate includes at least 5 of said rows and 7 of said columns of said grid openings.

10. The method of claim 6 wherein
said oppositely viewing slant-hole collimators include a left side slant-hole collimator viewing at a 20 degree angle to the right and a right side slant-hole collimator viewing at a 20 degree angle to the left; and
said imaging system includes an arrangement for sliding said slant-hole collimators along a plane with respect to said stationary object.

11. The method of claim 6 wherein
said container including said radioactive substance is rectangular in shape; and
said container is capable of being inserted into one of said grid openings in said grid localization plate.

12. The method of claim 6 wherein
said container including said radioactive substance is circular in shape;
said grid localization plate includes a cavity therein; and
said container is capable of being inserted into said cavity in said grid localization plate.

* * * * *